United States Patent
Pagnoulle et al.

(10) Patent No.: US 10,869,754 B2
(45) Date of Patent: Dec. 22, 2020

(54) FLEXIBLE INTRAOCULAR LENS INJECTION DEVICE AND STORAGE SHUTTLE FOR IMPLEMENTING SAME

(71) Applicant: PHYSIOL S.A., Liège (BE)

(72) Inventors: Christophe Pagnoulle, Verviers (BE); Dimitriya Bozukova, Liège (BE); Jean-Pascal Yves Delay, Ecully (FR); Julien Laurent Vidal, Lyons (FR)

(73) Assignee: PHYSIOL S.A., Liège (BE)

( * ) Notice: Subject to any disclaimer, the term of this patent is extended or adjusted under 35 U.S.C. 154(b) by 176 days.

(21) Appl. No.: 16/094,428

(22) PCT Filed: Apr. 19, 2017

(86) PCT No.: PCT/EP2017/059265
§ 371 (c)(1),
(2) Date: Oct. 17, 2018

(87) PCT Pub. No.: WO2017/182508
PCT Pub. Date: Oct. 26, 2017

(65) Prior Publication Data
US 2020/0038176 A1 Feb. 6, 2020

(30) Foreign Application Priority Data

Apr. 21, 2016 (BE) .................................. 2016/5271

(51) Int. Cl.
*A61F 2/16* (2006.01)
(52) U.S. Cl.
CPC ............ *A61F 2/1678* (2013.01); *A61F 2/167* (2013.01); *A61F 2/1691* (2013.01)

(58) Field of Classification Search
CPC .... A61F 2/1662; A61F 2/1664; A61F 2/1667; A61F 2/167; A61F 2/1672; A61F 2/1678
See application file for complete search history.

(56) References Cited

U.S. PATENT DOCUMENTS 5,772,666 A * 6/1998 Feingold ............... A61F 2/1664
606/107
6,203,549 B1 * 3/2001 Waldock ................. A61F 2/167
606/107

(Continued)

OTHER PUBLICATIONS

Written Opinion of the International Searching Authority dated Jul. 6, 2017, issued in corresponding International Application No. PCT/EP2017/059265, filed Apr. 19, 2017, 5 pages.

(Continued)

*Primary Examiner* — Wade Miles
(74) *Attorney, Agent, or Firm* — Christensen O'Connor Johnson Kindness PLLC

(57) ABSTRACT

A flexible intraocular lens injection device, comprising a tubular body that has a casing, a plunger, a barrel having a cross-section that decreases in the opposite direction to the tubular body, and a housing in the axial cavity of the tubular body intended to receive a storage shuttle containing a flexible intraocular lens, the casing of the tubular body having a side opening, so as to allow the insertion of the storage shuttle and in the vicinity of this side opening, the above-mentioned casing carrying a first outwardly-protruding rotary attachment means configured to engage with a second rotary attachment means provided on the storage shuttle, so that, when the two above-mentioned rotary attachment means are engaged, the storage shuttle is able to rotate about an axis of rotation parallel to said axial direction of the axial cavity of the tubular body.

8 Claims, 3 Drawing Sheets

(56) References Cited

U.S. PATENT DOCUMENTS

| | | | | |
|---|---|---|---|---|
| 2001/0020171 A1* | 9/2001 | Heyman | A61F 2/167 | |
| | | | 606/107 | |
| 2003/0036765 A1 | 2/2003 | Van Noy | | |
| 2004/0243141 A1* | 12/2004 | Brown | A61F 2/1678 | |
| | | | 606/107 | |
| 2005/0125000 A1* | 6/2005 | Tourrette | A61F 2/1678 | |
| | | | 606/107 | |
| 2006/0155299 A1* | 7/2006 | Waldock | A61F 2/1678 | |
| | | | 606/107 | |
| 2007/0060925 A1* | 3/2007 | Pynson | A61F 2/1664 | |
| | | | 606/107 | |
| 2007/0150054 A1* | 6/2007 | Pynson | A61F 2/1664 | |
| | | | 623/6.12 | |
| 2007/0150055 A1 | 6/2007 | Pynson | | |
| 2010/0130985 A1* | 5/2010 | Tanaka | A61F 2/1678 | |
| | | | 606/107 | |
| 2011/0190777 A1 | 8/2011 | Hohl | | |
| 2014/0066946 A1* | 3/2014 | Aguilera | A61F 2/1691 | |
| | | | 606/107 | |
| 2014/0135784 A1* | 5/2014 | Maroscheck | A61F 2/1678 | |
| | | | 606/107 | |
| 2014/0171956 A1* | 6/2014 | Helmy | G01M 11/081 | |
| | | | 606/107 | |
| 2014/0303636 A1* | 10/2014 | Valle | A61F 9/007 | |
| | | | 606/107 | |
| 2015/0272779 A1* | 10/2015 | Wagner | A61F 9/0017 | |
| | | | 606/107 | |
| 2015/0342730 A1 | 12/2015 | Messner et al. | | |
| 2016/0015562 A1* | 1/2016 | Nagasaka | A61F 2/167 | |
| | | | 606/107 | |
| 2016/0074155 A1* | 3/2016 | Raquin | A61F 2/1672 | |
| | | | 606/107 | |
| 2016/0175090 A1* | 6/2016 | Kobayashi | A61F 2/167 | |
| | | | 606/107 | |
| 2016/0250069 A1* | 9/2016 | Dockhom | A61F 2/1678 | |
| | | | 606/107 | |
| 2016/0331587 A1* | 11/2016 | Yamada | A61F 2/1678 | |
| 2018/0168800 A1* | 6/2018 | Kaegi | A61F 2/1678 | |

OTHER PUBLICATIONS

International Preliminary Report on Patentability dated Oct. 23, 2018, issued in corresponding International Application No. PCT/EP2017/059265, filed Apr. 19, 2017, 1 page.

International Search Report dated Jul. 6, 2017, issued in corresponding International Application No. PCT/EP2017/059265, filed Apr. 19, 2017, 2 pages.

* cited by examiner

FLEXIBLE INTRAOCULAR LENS INJECTION DEVICE AND STORAGE SHUTTLE FOR IMPLEMENTING SAME

This invention relates to a flexible intraocular lens injection device (or an injection device for a flexible intraocular lens, or a device for injecting a flexible intraocular lens), comprising a tubular body that has a casing and an axial cavity as well as a proximal end and a distal end, a plunger inserted into said axial cavity, at the above-mentioned proximal end, and movable in this cavity along an axial direction, a barrel arranged at said distal end of the tubular body and having an ejection cavity in communication with the axial cavity of the tubular body, this ejection cavity having a cross-section that decreases in the opposite direction to the tubular body, and a housing in the axial cavity of the tubular body intended to receive a storage shuttle containing a flexible intraocular lens.

Intraocular lenses (IOL) are intended to replace the eye's opacified lens (natural lens) in patients suffering from cataract, during a surgical operation. Cataract surgery is probably the most commonly practiced operation in humans, with a significant improvement in the sight in 98% of patients.

The technique in cataract surgery has made, in the last few years, enormous progress, thanks in particular to the decrease in the size of the incision through which the eye's lens is extracted and the synthetic lens implanted in the eye. The new flexible materials (silicones, flexible acrylics and hydrogels) allow for the implantation of the lens through an incision that is smaller than that made with the first rigid implants made from polymethyl methacrylate (PMMA). The flexible lens can indeed be implanted in a folded or wound conformation, before recovering, once installed in the eye and thanks to its particular viscoelastic properties (shape memory), its initial and final shape. The small incisions, without stitches, have the advantage of not causing any deformation of the cornea and therefore of preventing astigmatism. Recovering sight occurs faster and the refractive outcome is more stable.

The arrival of flexible lenses gave rise to the problem of installing these implants. This is because, in order to take advantage of a reduced incision, the lens has to be able to be folded and inserted into the eye in a wound form. A first known technique consists in implanting the lens using manual tweezers. The manipulation of the implant is however tedious. In addition, the incision has in this case a minimum length (about 3.2 mm) fixed by the thickness of the jaws of the tweezers and that of the folded implant.

An alternative implantation technique, increasingly widespread, consists in using an injection device suitable for flexible lenses. This injection device generally consists of two separate elements, a cartridge, on the one hand, and an injector, on the other hand (see for example U.S. Patent application 2005/0065534). The cartridge allows for the folding, winding and movement of the wound lens to an outlet orifice with a reduced diameter through which the implant is expelled into the eye, the injection of the lens through the cartridge being provided by a movement of the plunger of the injector in the manner of a syringe. In order to facilitate the movement of the implant in the cartridge, use is sometimes made of a plunger provided at its end with a cylindrical plug that can be inserted into a conduit of the cartridge, and a few drops of a lubricating additive are generally applied on the inner faces of the cartridge. This is generally a viscous product of the polysaccharide family (sodium hyaluronate, hydroxypropyl methyl cellulose, chondroitin sulphate, etc.) the usage of which is very widespread in ophthalmic surgery. The injection technique allows for the insertion of the implant into incisions with dimensions that can be less than 2 mm, while contributing to a simplification and a securing of the implantation procedure.

Many variants of such cartridges are currently available and have an orifice suitable for different sizes of incision with a circular or polygonal shape. The main inherent limit with these cartridges relates to the manual operation of positioning the lens (loading) in the loading chamber. The lens to be implanted must be removed from its packaging and correctly placed in the cartridge. The lens is first positioned flat within the loading chamber using tweezers and by exerting a vertical force on the implant. The cartridge is then closed manually, by ovalising the implant (pre-winding). During this operation of loading the lens, the risk of pinching and of damaging the implant during the closing is very high.

Very recently, devices for injecting intraocular lenses, preloaded with a flexible lens, have been developed (see for example EP-A-1481652). These integrated injection systems, cartridge and injector forming a single and unique device, are also used for packaging the lens and eliminate the operation of manually loading the implant into the cartridge and all of the constraints relating to this manipulation. Having recourse to a preloaded device saves a substantial amount of time during the surgical act and contributes to a safer implantation. The sources of contamination of the lens are greatly reduced, as the contacts between the fingers of the surgeon and the implant are eliminated. Although these devices are undeniably a technological breakthrough, it is still the case that they all have many limits.

One of the major difficulties is to allow for both the storage of the lens in a non-stressed position (flat) and for its winding at the time of implantation under the action of the plunger, and this without damaging the implant. The lens indeed tends to wind itself around the end of the plunger during injection, which can hinder the expulsion of the implant into the eye and damage the lens.

One solution consists in using a mechanism for pre-folding the lens that is very sophisticated and incorporated into the injector. In this way, the lens can be pre-folded mechanically, before actuating the plunger, which prevents a pinching of the lens by the plunger (see for example FR-A-2808993). The pre-folding mechanisms considered however do not perform very well and are sources of failure.

Another limit of these pre-loaded and integrated systems (injector and cartridge), closely relating to the technological constraints mentioned hereinabove, lies in the size of the incision, generally greater than 3.0 mm.

Another potential design problem is to be taken into consideration in the specific case of hydrophilic intraocular lenses (hydrogels). The latter are sterilised in the vapour phase and must imperatively be stored in an aqueous medium in order to guarantee the hydration rate and the mechanical flexibility of the material. The integrated pre-loaded injection system is therefore sterilised in the vapour phase and delivered immersed in an aqueous solution, which makes the handling of the device very hazardous at the time of implantation (wet surface and difficult grasping) and can also lead to problems in selecting the materials involved in the designing of the injector (compatibility with vapour sterilisation).

Finally, devices are known for injecting intraocular lenses that comprise the two elements separately, cartridge and injector, the cartridge being pre-loaded with the intraocular lens to be injected in a container filled with a sterile liquid. More precisely, the cartridge typically comprises two welded parts or a single piece: a barrel (or endpiece) for the expulsion of the lens and a storage chamber (or storage shuttle). During the storage thereof, the intraocular lens is in the storage chamber (or loading chamber) of the cartridge and is not in the stressed condition: it retains its flexibility thanks to the liquid of the container. In these devices, the cartridge is taken from its container using directly or indirectly the injection device itself, and after taking, under the thrust of the plunger of the device, the lens is wound around itself before being ejected into the eye of a patient (see for example BE-1016692, WO 2006/070219 and WO 2013/038021). In BE-1016692, the ejection endpiece (or barrel) of the device is retained in the sterile container, which is not very desirable, because the liquid of the container may attack the material used in this endpiece (or barrel) and in particular for a material for internally covering the barrel which allows for easier sliding of the lens along the barrel. Patent applications WO 2006/070219 and WO 2013/038021 disclose extremely complex devices, of expensive manufacture and requiring the implementation of mechanisms that are likely to have weaknesses during the handling. Both require handling the ejection endpiece (or barrel) which is a particularly fragile part of the device and outside contamination of which must be avoided at all costs.

SUMMARY OF THE INVENTION

This invention has for purpose to overcome the aforementioned disadvantages and to develop a simple intraocular lens injection device wherein a storage shuttle containing the lens pre-loaded in a non-stressed position can be taken from a sterile container and loaded into the body of the device simply and quickly and without risk of contaminating or damaging the injection endpiece (or barrel) of the device. In the latter, in the loaded state, the lens must be able to be expelled from the storage shuttle in the wound state, without risk of damage.

These problems are resolved according to the invention by an injection device as described in the preamble, wherein the casing of the tubular body has a side opening and wherein the above-mentioned casing carries a first outwardly-protruding rotary attachment means.

Preferably, said side opening gives access from the outside to said housing, so as to allow the insertion of the storage shuttle into the latter.

Preferably, the first rotary attachment means is capable of cooperating with a second rotary attachment means provided on the storage shuttle, so that to allow, in cooperation position of the two above-mentioned rotary attachment means, a rotation of the storage shuttle around an axis of rotation parallel to said axial direction of the axial cavity of the tubular body, between a first position of the storage shuttle where it is outside the tubular body and a second position of the storage shuttle where it is loaded in the above-mentioned housing.

In this device, a side opening is sufficient in the tubular body to give access to the receiving housing of the storage shuttle. The rotary attachment means allow for a rotation of the storage shuttle without problem from the outside into the receiving housing about an axis parallel to the axial direction of the movement of the plunger, i.e. parallel to the axis of the tubular body. The angle of rotation can preferably have a value between 90° and 180°. In this housing the storage shuttle is ready for the expulsion of the lens in the endpiece (or barrel) under the thrust of the plunger which can be actuated by an operator. In such an embodiment the tubular body, the endpiece, the side opening and the first rotary attachment means can be made of a synthetic material, in particular by moulding, without requiring, for the manufacture of the device per se, an assembly of many parts via complex means such as latches, pivot buttons, snap-fitting tabs, etc. The endpiece (or barrel) is already in place before the insertion of the storage shuttle and therefore no longer needs to be handled after the insertion of the storage shuttle into the tubular body. Finally the endpiece can be retained with the injection device, dry, and not in a sterile aqueous medium that risks damaging it.

According to an embodiment of the invention, the casing of the tubular body carries, as a first rotary attachment means, a hollow cylinder that has a longitudinal axis parallel to said axial direction, and into which can be pressed a rod provided on the storage shuttle, as a second rotary attachment means. According to another embodiment of the invention the casing of the tubular body carries, as a first rotary attachment means, a rod axially parallel to said axial direction, and around which can be pressed a hollow cylinder provided on the storage shuttle, as a second rotary attachment means. In these embodiments the two rotary attachment means together form the elements of a hinge which are both arranged protruding on their respective supports and therefore allowing for particularly easy manufacture and engagement cooperation via simple pressing of one means of attaching into the other.

According to a particular embodiment of the invention the housing in the axial cavity of the tubular body has first snap-fastening means capable of cooperating with second snap-fastening means provided on the storage shuttle in such a way as to block the storage shuttle in its above-mentioned second position. Once inserted into the receiving housing, the storage shuttle is as such blocked therein and can no longer be moved out of the position wherein it is ready for the expulsion of the lens into the endpiece under the thrust of the plunger.

Preferably, the casing carries the first outwardly-protruding rotary attachment means in the vicinity of the side opening. Preferably, this means that the first rotary attachment means is at the same location along the axial direction as the side opening and the housing. This will be understood more clearly through the drawings.

This invention also relates to a storage shuttle to be inserted into an injection device a flexible intraocular lens according to the invention. This storage shuttle comprises
    a shuttle body having a shuttle cavity intended to receive a flexible intraocular lens,
    an outlet opening, which is intended, in the above-mentioned second position of the storage shuttle, to allow for a communication between the shuttle cavity and the injection cavity of the endpiece, and
    an inlet opening, which is intended, in the above-mentioned second position of the storage shuttle, to allow for a communication between the shuttle cavity and the axial cavity of the tubular body wherein said plunger is, and
    the shuttle body outwardly-protruding carries said second rotary attachment means capable of cooperating with said first rotary attachment means carried by the casing of the tubular body.

Preferably, the shuttle body outwardly carries said second snap-fastening means capable of cooperating with said first snap-fastening means of the housing of the tubular body of the injection device according to a preferred alternative described, in order to block the storage shuttle in its second position.

Preferably, the storage shuttle has a gripping means to be grasped in order to actuate said rotation of the storage shuttle between its first position and its second position.

Preferably the storage shuttle according to the invention is stored in a sterile container. The inventors also propose such a sterile container comprising a storage shuttle such as described hereinabove.

Advantageously, during the storage of the storage shuttle, said sterile container is provided with a closeable opening. It is more preferably filled with a sterile aqueous medium.

According to a particular embodiment the sterile container has a storage shuttle retaining portion wherein the shuttle body is held with the inlet opening of the storage shuttle and said second rotary attachment means of the latter, oriented towards the closeable opening of the container, and a pushing portion intended to receive the tubular body of the injection device, provided with its barrel, in such a way that, in the position of pushing of said tubular body into this pushing portion, said first rotary attachment means thereof cooperates with said second rotary attachment means of the storage shuttle, thus allowing a taking of the storage shuttle outside the container. In this container, the injection device the intraocular lens according to the invention can be pressed with son barrel arranged at the distal end of the tubular body, without risk of damaging it. Furthermore the storage shuttle can be taken from the container and brought into the receiving housing of the storage shuttle, without handling the endpiece (or barrel).

According to an advantageous embodiment of the invention, the retaining portion of the storage shuttle in the container has a ribbed bottom allowing for a passage of the above-mentioned liquid through the outlet opening of the storage shuttle as well as through the inlet opening of the latter. In this way the intraocular lens made of flexible material is fully immersed in the sterile aqueous medium.

This invention also relates to a method for loading a storage shuttle according to the invention into an injection device an intraocular lens according to the invention. This method comprises the following steps:

opening the sterile container containing the storage shuttle provided with a flexible intraocular lens, inserting the tubular body of the injection device, provided with its barrel, into said pushing portion of the sterile container, with cooperation between the first rotary attachment means of the tubular body and the second rotary attachment means of the storage shuttle, taking outside the container the tubular body and the storage shuttle attached to one another, rotation the storage shuttle between its above-mentioned first position outside the tubular body and its above-mentioned second position where it is loaded inside the above-mentioned housing of the tubular body through the above-mentioned side opening provided in the tubular body, the intraocular lens being in this second position of the storage shuttle ready to be moved and wound under the thrust of the plunger into the ejection cavity of the endpiece, and then ejected outside.

Other details and particularities of the invention are to be taken from the accompanying claims.

BRIEF DESCRIPTION OF THE FIGURES

This invention will now be described in more detail in reference to drawings, which show in a non-limiting way an embodiment according to the invention.

In the various drawings, identical or similar elements are designated by the same references.

DETAILED DESCRIPTION OF CERTAIN EMBODIMENTS OF THE INVENTION

Figures 1, 2:
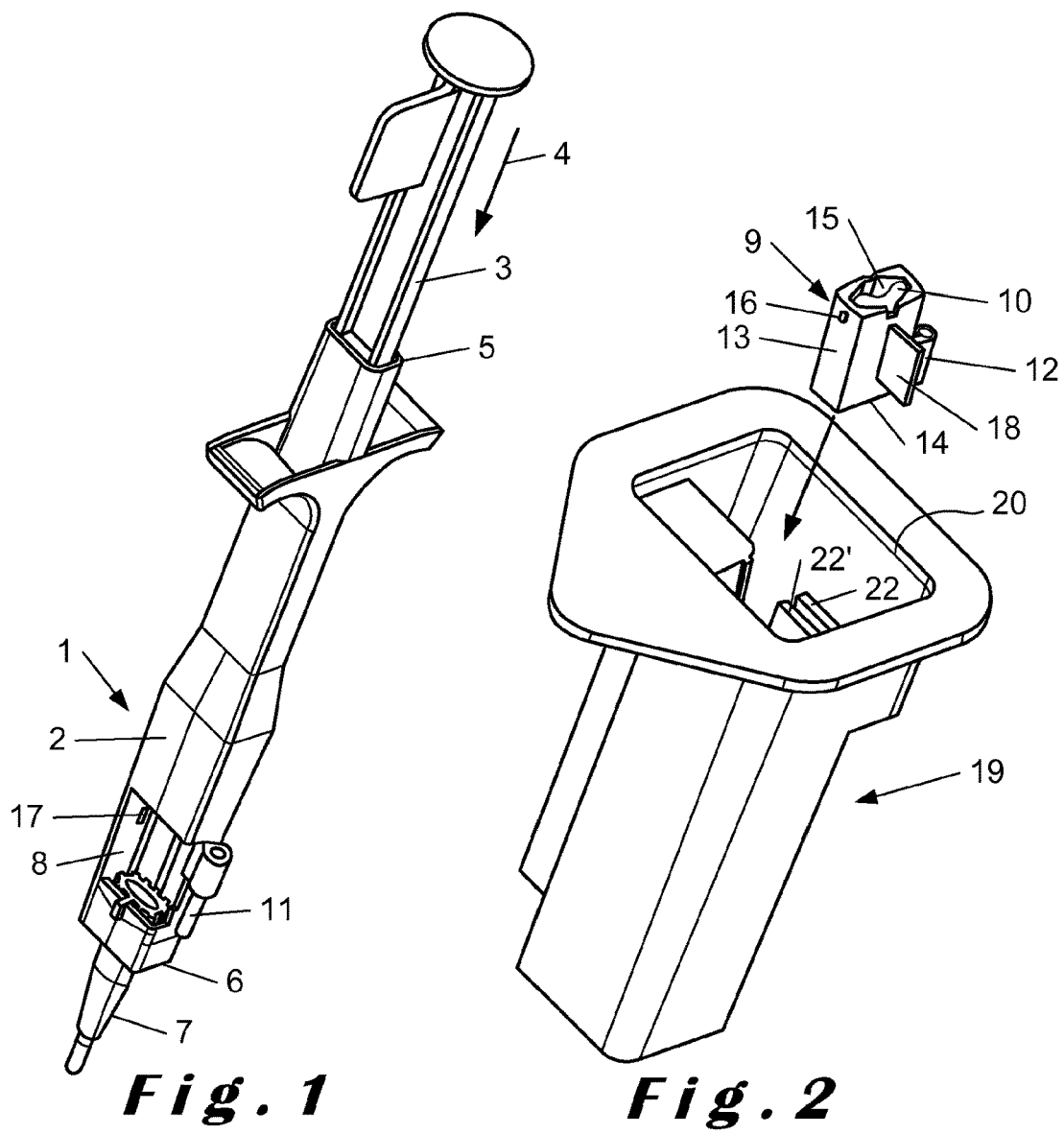
FIG. 1 is a perspective view of an injection device according to the invention, without storage shuttle.
FIG. 2 is a perspective view of a container containing a storage shuttle, after detaching the seal closing this container.

As can be seen in FIG. 1 the injection device shown comprises a tubular body 1 that has a casing 2 enclosing an axial cavity wherein a plunger 3 can slide along an axial direction 4. The plunger 3 is inserted into the axial cavity at the proximal end 5 of the tubular body 1. At the distal end 6 of the latter is arranged a barrel 7 which has an ejection cavity in communication with the axial cavity of the tubular body 1. This ejection cavity has a cross-section that decreases in the opposite direction to the tubular body and is open to the outside at the free end of the barrel 7.

The injection device shown also comprises a housing 8 in the axial cavity of the tubular body 1 which is intended to receive a storage shuttle 9 containing a flexible intraocular lens 10 (see FIG. 2).

According to the invention the casing 2 of the tubular body 1 has, as shown in FIG. 1, a side opening that gives access to the housing 8 from the outside. Via this opening the storage shuttle 9 can be inserted into the device. In the vicinity of this opening, more particularly at the edge thereof, the casing 2 carries a first outwardly-protruding rotary attachment means, shown here in the form of a cylindrical rod 11, that has a longitudinal axis parallel to the axial direction 4 of the plunger 3.

This cylindrical rod 11 is arranged so as to be able to engage with a second rotary attachment means, provided outwardly-protruding on the storage shuttle 9. In the embodiment shown, this second rotary attachment means is a hollow cylinder 12 capable of engaging with the cylindrical rod 11 by pressing, while still allowing for a rotation of the storage shuttle in relation to the injection device. Pressed one into the other, the rod 11 and the hollow cylinder 12 form a usual hinge exit.

The storage shuttle 9 has a shuttle body 13 that carries this outwardly-protruding hollow cylinder 12 and which is provided with a cavity intended to receive the flexible intraocular lens 10 in a non-stressed state. The storage shuttle 9 has an outlet opening 14 intended to allow for a communication between the cavity of the storage shuttle 9 and the ejection cavity of the barrel 7, when the storage shuttle 9 is loaded into the housing 8 of the injection device. The storage shuttle 9 also has an inlet opening 15 which, in this position of the storage shuttle 9, allows for communication with the axial cavity of the tubular body 1 of the device.

In the example shown, the shuttle body 13 is provided with a lug 16 protruding outwards. This lug 16 is arranged in such a way that, in the position of loading of the storage shuttle in the housing 8, it snap-fits into a recess 17 of the casing 2 in such a way as to block the storage shuttle in this housing. Other snap-fitting means usual for those skilled in the art can of course be considered instead of this lug 16 and this recess 17.

The shuttle body 13 also carries on one of its faces a tab 18 that is used as a gripping means in order to grasp the storage shuttle 9 and pivot it about the rod 11 of the tubular body between a first position, located outside the tubular body 1, and a second position located inside the housing 8.

Figure 3:
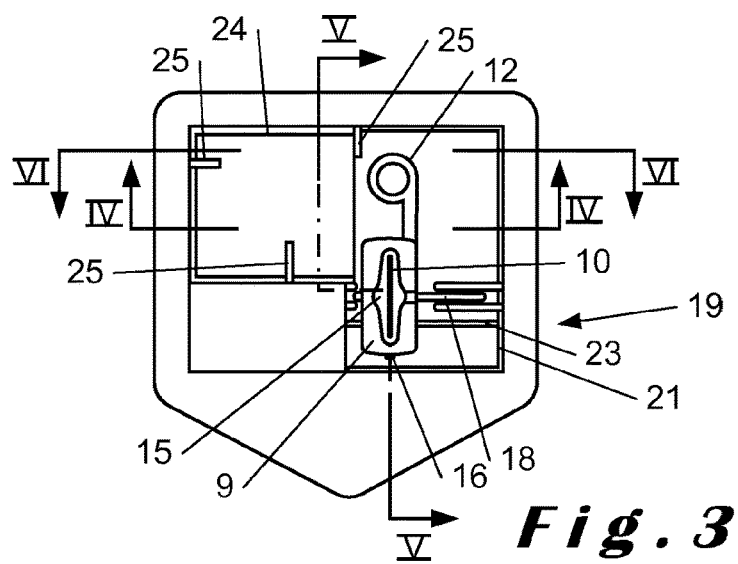
FIG. 3 shows a top view of the container according to FIG. 2.
Figure 6:
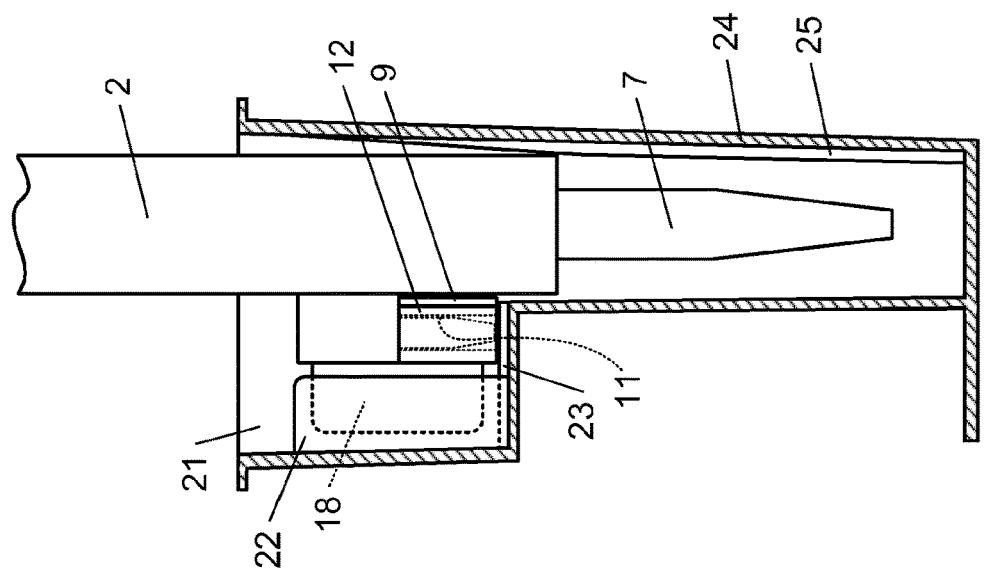
FIG. 6 shows a cross-section view along the line VI-VI of FIG. 3 where the storage shuttle is a position of cooperation with the tubular body of the injection device pressed into the sterile container.
Figure 5:
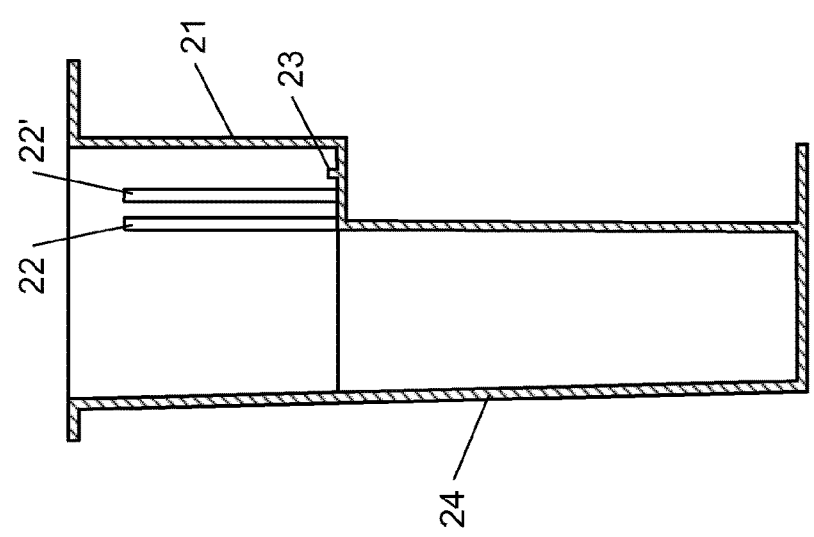
FIG. 5 shows a cross-section view along the line V-V of FIG. 3.
Figure 4:
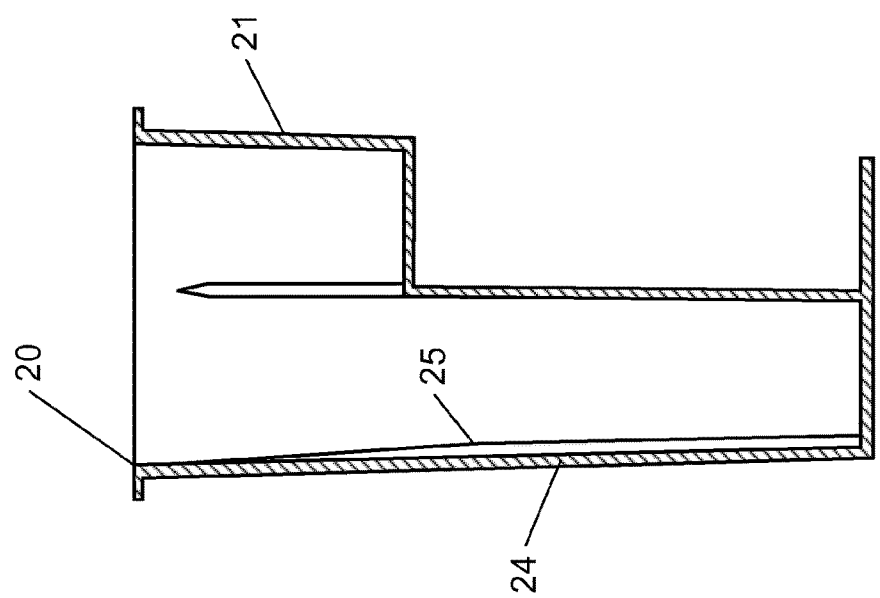
FIG. 4 shows a cross-section view along the line IV-IV of FIG. 3.

As shown in FIGS. 2 and 3, the storage shuttle 9 is retained in a sterile container 19, that has an opening 20 closeable for example by a detachable seal not shown. In the sealed state, the sterile container contains a suitable sterile aqueous medium so that the intraocular lens 10 retains its flexibility.

The container 19 of the example shown comprises a storage shuttle retaining portion 21 wherein the shuttle body is held with the inlet opening 15 and the hollow cylinder 12 oriented upwards, i.e. towards the closeable opening of the container. In order to guide the insertion of the storage shuttle into this retaining portion 21, the container comprises guides 22, 22' between which the gripping tab 18 can slide. The bottom of this retaining portion can be provided with one or more ribs 23. This arrangement favours the circulation of the sterile aqueous medium in the storage shuttle 9 via the inlet opening 15 as well as via the outlet opening 14 thereof, when the storage shuttle 9 is retained in the sterile container 19.

The container 19 of the example shown further comprises a pushing portion 24 for the injection device provided with its barrel 7. In the pushing position the rod 11 is pushed into the hollow cylinder 12 carried by the storage shuttle 9. In order to facilitate this pushing, guide ribs 25 lead the two rotary attachment elements 11 and 12 to engage perfectly. The barrel 7 (or endpiece), already in place on the injection device, thus does not come into contact with the walls of the container and does not reach the bottom of the pushing portion. The insertion thereof into the container is carried out therefore without risk of damage, or contamination.

Figures 7, 8:
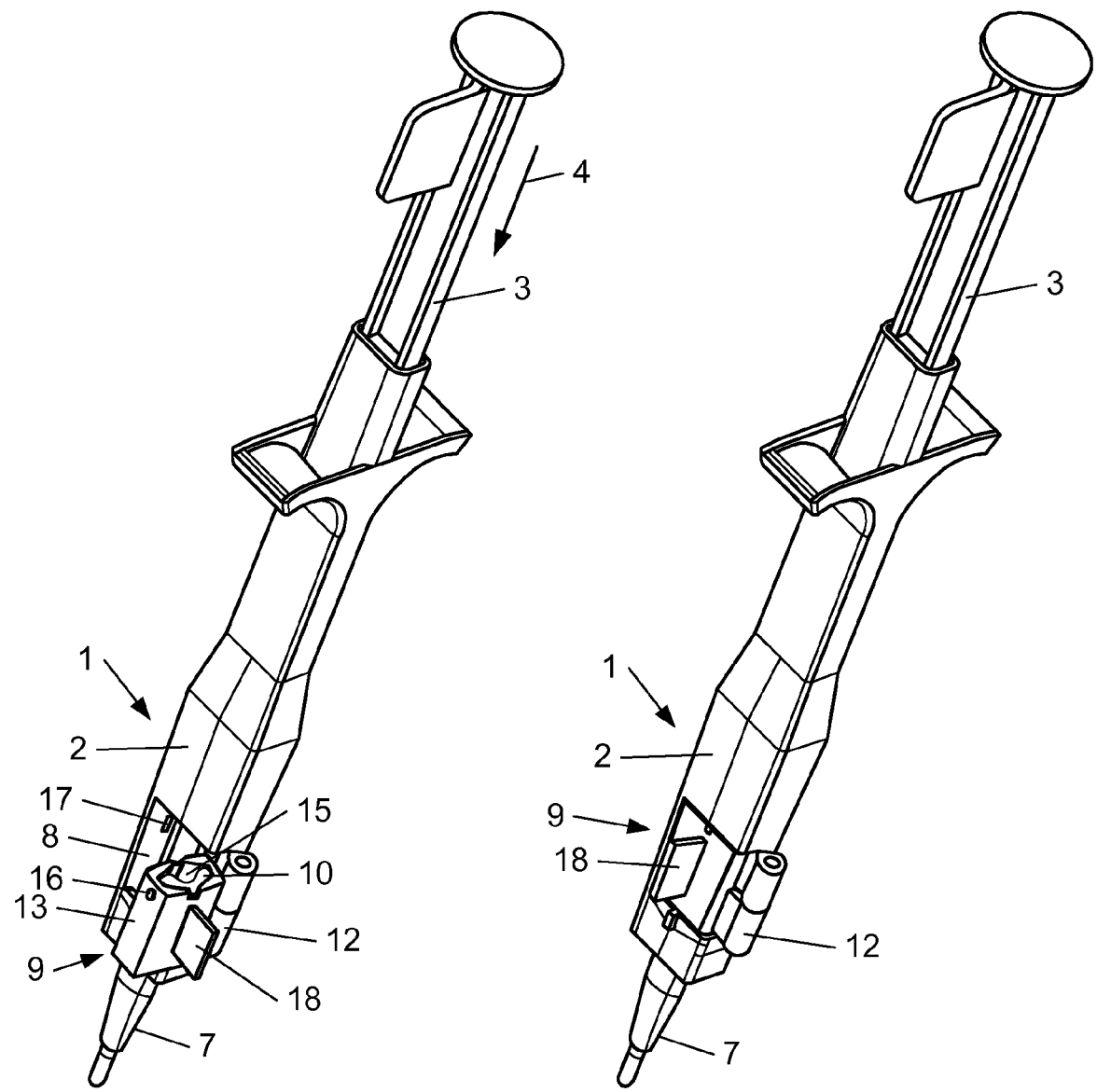
FIGS. 7 and 8 are perspective views of the injection device according to FIG. 1, with the storage shuttle respectively in its first position and in its second position.

When the injection device is extracted from the sterile container 19, it carries with it the storage shuttle 9, which is then in the position shown in FIG. 7.

The operator then grasps the gripping tab 18 and pivots the storage shuttle 9 in the housing 8, wherein it is blocked by the snap-fastening means 16 and 17.

In this snap-fitting position, the inlet opening 15 of the storage shuttle communicates with the axial cavity of the tubular body 1. The operator can then press on the plunger 3, which at its distal end is advantageously provided with a cushion made of flexible material in order to not damage the lens. Under the action of the plunger the lens 10 is then pushed through the outlet opening 14 of the storage shuttle into the ejection cavity of the barrel 7. The latter, having a decreasing transversal section in the direction of the free end of the barrel 7, forces the lens to wind around itself, which makes it possible to eject it in this wound form into the eye of the patient.

It must be understood that the invention is in no way limited to this embodiment and that many modifications or alternatives can be made thereto in the scope of the accompanying claims.

The invention claimed is:

1. A flexible intraocular lens injection device, comprising:
   a tubular body having a casing and an axial cavity, the tubular body also having a proximal end and a distal end;
   a plunger inserted into said axial cavity, at the proximal end, and movable in the axial cavity along an axial direction;
   a barrel arranged at said distal end of the tubular body and having an ejection cavity in communication with the axial cavity of the tubular body, the ejection cavity having a cross-section that decreases in the opposite direction to the tubular body; and
   a housing in the axial cavity of the tubular body for receiving a storage shuttle containing a flexible intraocular lens;
   wherein the casing of the tubular body has a side opening, which provides access from the outside to said housing, so as to allow the insertion of the storage shuttle into the housing, and wherein the casing carries a first outwardly-protruding rotary attachment configured to cooperate with a second rotary attachment provided on the storage shuttle, so that when in cooperation, the storage shuttle is configured to rotate around an axis of rotation parallel to said axial direction of the axial cavity of the tubular body, between a first position of the storage shuttle where it is outside the tubular body and a second position of the storage shuttle where it is loaded in the housing.

2. The injection device according to claim 1, wherein the first rotary attachment comprises a hollow cylinder having a longitudinal axis parallel to the axial direction, wherein the casing of the tubular body carries the hollow cylinder, the second rotary attachment provided on the storage shuttle configured to be pressed into the hollow cylinder.

3. The injection device according to claim 1, wherein the first rotary attachment comprises a rod having a longitudinal axis parallel to the axial direction, wherein the casing of the tubular body carries the rod, the second rotary attachment provided on the storage shuttle configured to be pressed around the rod.

4. The injection device according to claim 1, wherein the housing in the axial cavity of the tubular body has a first snap fastener configured to cooperate with a second snap fastener provided on the storage shuttle in such a way as to block the storage shuttle in the second position.

5. An injection assembly comprising:
   the injection device according to claim 1; and
   a storage shuttle comprising
      a shuttle body having a shuttle cavity for receiving a flexible intraocular lens;
      an outlet opening configured to allow for communication between the shuttle cavity and the ejection cavity of the barrel of the injection device; and an inlet opening configured to allow for communication between the shuttle cavity and the axial cavity of the tubular body of the injection device; and
   wherein the shuttle body carries a second rotary attachment capable of cooperating with the first rotary attachment carried by the casing of the tubular body.

6. The injection assembly according to claim 5, wherein the shuttle body outwardly carries a second snap fastener configured to cooperate with a first snap fastener of a housing of the tubular body, in order to block the storage shuttle in the second position.

7. The injection assembly according to claim 5, further comprising gripping means to be grasped in order to actuate a rotation of the storage shuttle between the first position and the second position.

8. A method for loading a storage shuttle into a flexible intraocular lens injection device comprising:
- providing the flexible intraocular lens injection device according to claim 1;
- opening a sterile container containing a storage shuttle provided with a flexible intraocular lens;
- inserting the tubular body of the injection device, provided with the barrel, into a pushing portion of the sterile container, with cooperation between the first rotary attachment of the tubular body and a second rotary attachment of the storage shuttle to attach the tubular body and the storage shuttle to one another;
- removing the tubular body and the storage shuttle attached to one another from the sterile container;
- rotating the storage shuttle between the first position outside the tubular body and a second position where it is loaded inside the housing of the tubular body through the side opening provided in the tubular body, the intraocular lens being in this second position of the storage shuttle ready to be moved and wound under the thrust of the plunger into the ejection cavity of the barrel, and then ejected outside.

\* \* \* \* \*